United States Patent
Alanine et al.

[11] Patent Number: 5,952,344
[45] Date of Patent: Sep. 14, 1999

[54] TETRAHYDROISOQUINOLINE DERIVATIVES

[75] Inventors: Alexander Alanine, Riedisheim; Anne Bourson, Mulhouse, both of France; Bernd Büttelmann, Schopfheim; Günther Fischer, Lörrach-Brombach, both of Germany; Marie-Paule Heitz Neidhart, Hagenthal le Bas, France; Vincent Mutel, Mulhouse, France; Emmanuel Pinard, Saint Louis, France; Stephan Röver, Inzlingen; Gerhard Trube, Rheinfelden, both of Germany; René Wyler, Zürich, Switzerland

[73] Assignee: Hoffmann-La Roche Inc., Nutley, N.J.

[21] Appl. No.: 09/008,724

[22] Filed: Jan. 19, 1998

Related U.S. Application Data

[63] Continuation of application No. 08/789,351, Jan. 27, 1997, abandoned.

[30] Foreign Application Priority Data

Feb. 3, 1996 [EP] European Pat. Off. .............. 96101553

[51] Int. Cl.[6] .................................................... A61K 31/47
[52] U.S. Cl. ........................... 514/307; 514/291; 514/309
[58] Field of Search ..................... 546/141, 142, 546/146, 147, 149, 90; 514/307, 309, 291

[56] References Cited

U.S. PATENT DOCUMENTS

| | | | |
|---|---|---|---|
| 3,480,714 | 11/1969 | Werner et al. | 424/258 |
| 3,509,158 | 4/1970 | Dobson et al. | 260/287 |
| 3,803,151 | 4/1974 | Conway et al. | 260/285 |
| 3,823,148 | 7/1974 | Jansen et al. | 260/289 R |
| 4,689,330 | 8/1987 | Janssens et al. | 514/321 |
| 4,774,248 | 9/1988 | Lafon et al. | 514/269 |
| 5,011,834 | 4/1991 | Weber et al. | 514/212 |
| 5,192,751 | 3/1993 | Thor | 514/82 |
| 5,389,638 | 2/1995 | DeBernardis et al. | 514/291 |
| 5,439,915 | 8/1995 | Commons et al. | 514/292 |

FOREIGN PATENT DOCUMENTS

| | | |
|---|---|---|
| 91868 | 8/1977 | Japan . |
| 41481 | 2/1995 | Japan . |
| 976 829 | 2/1962 | United Kingdom . |
| WO 91/17156 | 11/1991 | WIPO . |
| WO 97/23458 | 7/1997 | WIPO . |

OTHER PUBLICATIONS

Cook, et al. J. Med. Chem. 1995, pp. 753–763, 1995.
Abstract corresponding to JP 91868, 1977.
Abstract corresponding to JP 41481, 1995.
Ohkubo et al., Chem. Pharm. Bull. 44(1) pp. 95–102 (1996).
Brossi et al., Chim. Acta vol. 43, pp. 1459–1472 (1960).
Helv. Chim. Acta vol. 43, pp. 1459–1472 (1960).
Chem. Abstracts vol. 77, No. 1/ 7/3/72 Abstr. No. 5364 (1972).
Chem. Pharm. Bull. 44(4) pp. 778–784 (1996).
Psychopharmacology 1995, 117, pp. 172–177.
Brain Research 735, 1996 pp. 67–82.
Eur. Jour. of Pharmacology, 247, 1993 pp. 319–324.
Yin et al., Chemical Abstracts 122:105626, 1995.
Sheppard et al., Molecular Pharmacology, 12(5), pp. 854–861, 1976.
Damasio, Alzheimer's Disease and related dementias, Cecil Textbook of Medicine, vol. 2, 20th Edition, pp. 1992–1996, 1996.
Jankovic, The Extrapyramidal Disorders, Cecil Textbook of Medicine, vol. 2, 20th edition, pp. 2042–2046, 1996.

*Primary Examiner*—Richard L. Raymond
*Assistant Examiner*—Deepak R. Rao
*Attorney, Agent, or Firm*—George W. Johnston; Patricia S. Rocha-Tramaloni; Robert A. Silverman

[57] ABSTRACT

The present invention relates to the use of tetrahydroisoquinoline derivatives of the general formula

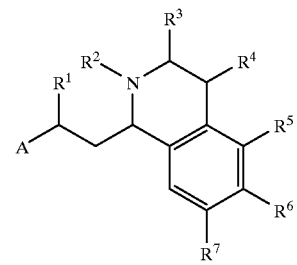

I wherein
A is aryl
$R^1$ is hydrogen, hydroxy, lower alkyl, lower alkoxy, R—CO— or R—COO—, wherein R is lower alkyl;
$R^2$ is hydrogen, lower alkyl or cycloalkyl
$R^3$–$R^7$ are independently hydrogen, lower alkyl, lower alkoxy, hydroxy or
$R^3$ and $R^4$ taken together are —$(CH_2)_n$— or
$R^6$ and $R^7$ taken together are —$OCH_2O$— and
n is 3 or 4,
as well as pharmaceutically acceptable salts for the manufacture of medicaments for the control or treatment of diseases which represent therapeutic indications for NMDA receptor subtype specific blockers.

11 Claims, No Drawings

TETRAHYDROISOQUINOLINE DERIVATIVES

This is a continuation of application Ser. No. 08/789,351, filed Jan. 27, 1997, now abandoned.

BACKGROUND OF THE INVENTION

U.S. Pat. Nos. 3,238,212, 3,067,203 and 3,217,007 (incorporated herein by reference) describe isoquinoline derivatives and their salts as possessing analgesic, spasmolytic and antitussive activities. Mol. Pharmacol. (1976), 12(5), 854–61 describes tests of tetrahydroisoquinolines for agonist and antagonist activity with dopamine and beta adenylate cyclase system.

NMDA receptors have a key function in modulating neuronal activity and plasticity which makes them key players in mediating processes underlying development of CNS as well as learning and memory formation. Under pathological conditions of acute and chronic forms of neurodegeneration overactivation of NMDA receptors is a key event for triggering neuronal cell death.

NMDA receptors are composed of members from two subunit families, namely NR-1 (8 different splice variants) and NR-2 (A to D) originating from different genes. Members from the two subunit families show a distinct distribution in different brain areas. Heteromeric combinations of NR-1 members with different NR-2 subunits result in NMDA receptors, displaying different pharmacological properties.

Therapeutic indications for NMDA receptor subtype specific blockers include acute forms of neurodegeneration caused for example by stroke and brain trauma, and chronic forms of neurodegeneration such as Alzheimer's disease, Parkinson's disease, Huntington's disease, ALS (amyotrophic lateral sclerosis) and neurodegeneration associated with bacterial or viral infections, and, in addition, therapeutic indications such as schizophrenia, anxiety and depression.

BRIEF SUMMARY OF THE INVENTION

The invention relates to compounds of the formula

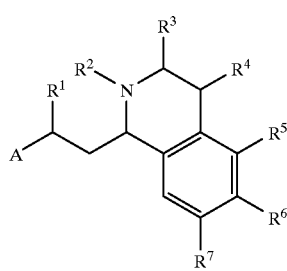

I wherein
A is aryl
$R^1$ is hydrogen, hydroxy, lower alkyl, lower alkoxy, R—CO— or R—COO—, wherein R is lower alkyl;
$R^2$ is hydrogen, lower alkyl or cycloalkyl
$R^3$–$R^7$ are, independently, hydrogen, lower alkyl, lower alkoxy, hydroxy or
$R^3$ and $R^4$ taken together are —(CH$_2$)$_n$— or
$R^6$ and $R^7$ taken together are —OCH$_2$O— and
n is 3 or 4, and pharmaceutically acceptable salts thereof.

It has surprisingly been found that compounds of formula I, and pharmaceutically acceptable salts thereof, are NMDA-R subtype selective blockers.

Compounds of formula I and pharmaceutically acceptable salts thereof are therefore useful in the treatment of acute forms of neurodegeneration caused for example by stroke and brain trauma, and chronic forms of neurodegeneration such as Alzheimer's disease, Parkinson's disease, Huntington's disease, ALS and neurodegeneration associated with bacterial or viral infections, and, in addition, therapeutic indications such as schizophrenia, anxiety and depression.

One aspect of the present invention relates to a method of treating or preventing diseases caused by overactivation of NMDA receptor subtypes, which comprises administering to a host in need of such treatment an effective amount of a compound of formula I or a pharmaceutically acceptable salts thereof. Examples of diseases caused by over reaction of NMDA-R receptor subtypes include acute forms of neurodegeneration caused, for example, by stroke and brain trauma, and chronic forms of neurodegeneration such as Alzheimer's disease, Parkinson's disease, Huntington's disease, ALS and neurodegeneration associated with bacterial or viral infections, and, in addition, therapeutic indications such as schizophrenia, anxiety and depression.

Another aspect of the present invention relates to compounds of formula

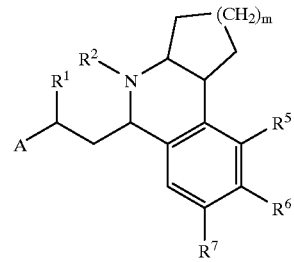

Ia wherein A, $R^1$, $R^2$ and $R^5$-$R^7$ are described as above and m is 2.

DETAILED DESCRIPTION OF THE INVENTION

The following definitions of the general terms used in the present description apply irrespective of whether the terms in question appear alone or in combination.

As used herein, the term "lower alkyl" denotes a straight or branched-chain alkyl group containing from 1 to 4 carbon atoms, for example, methyl, ethyl, propyl, isopropyl, butyl and the like. The term "aryl" denotes an aromatic hydrocarbon residue, preferably phenyl, which may be unsubstituted or substituted by one or more (up to three) substitutents, selected from hydroxy, lower alkyl, halogen, lower alkoxy or nitro.

The term "halogen" denotes chlorine, iodine, fluorine or bromine. The term "lower alkoxy" denotes an alkyl group, as defined earlier, which is attached via an oxygen atom. The term "cycloalkyl" denotes saturated cyclic hydrocarbon residues containing 3 to 6 carbon atoms.

The tetrahydroisoquinoline compounds of formula I contain two asymmetric carbon atoms. Accordingly, the formation of two stereoisomeric racemates is possible. The present invention embraces all possible racemates and their optical antipodes.

Preferred compounds of formula I are compounds in which $R^1$ is hydrogen or hydroxy. Also preferred are compounds of formula I in which $R^2$ is lower alkyl, preferably methyl, or hydrogen. Also preferred are compounds of formula I in which $R^3$ and $R^4$ are hydrogen or taken together are —(CH$_2$)$_n$—, where n is preferably 4. Also preferred are compounds of formula I in which $R^6$ and $R^7$ are lower alkoxy, preferably methoxy, or hydroxy.

In preferred compounds of formula I other than compounds of formula Ia, $R^3$, $R^4$ and $R^5$ are hydrogen. In preferred compounds of formula Ia $R^5$ is hydrogen.

Exemplary preferred compounds are:

2-(6,7-Dimethoxy-2-methyl-1,2,3,4-tetrahydroisoquinolin-1-yl)-1-p-tolyl-ethanol;

1-[2-(4-Chloro-phenyl)-ethyl]-6-methoxy-2-methyl-1,2,3,4-tetrahydroisoquinolin-7-ol;

1-(4-Chloro-phenyl)-2-(6,7-dimethoxy-2-methyl-1,2,3,4-tetrahydroisoquinolin-1-yl)-ethanol;

1-[2-(4-Chloro-phenyl)-ethyl]-2-methyl-1,2,3,4-tetrahydro-isoquinoline-6,7-diol;

6,7-Dimethoxy-2-methyl-1-(2-p-tolyl-ethyl)-1,2,3,4-tetrahydroisoquinoline;

6-[2-(4-Chloro-phenyl)-ethyl]-8,9-dimethoxy-5-methyl-1,2,3,4,4a,5,6, 10b-octahydro-phenanthridine;

2-(6,7-Dimethoxy-2-methyl-1,2,3,4-tetrahydroisoquinolin-1-yl)-1-(4-nitro-phenyl)-ethanol; and 6-[2-(4-Chloro-phenyl)-ethyl]-8,9,dimethoxy-1,2,3,4,4a,5,6, 10b-octahydro-phenanthridine.

Compounds of formula I can be prepared by known processes, described for example, in U.S. Pat. Nos. 3,238, 212 or 3,217,007, which describe a process which comprises reacting a dihydroisoquinolinium compound of the formula

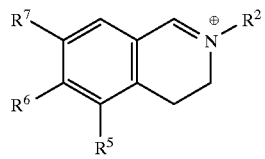

II wherein $R^2$ and $R^5$–$R^7$ are as described above, with a ketone having the formula CH$_3$COA, wherein A is as described above, in the presence of a basic condensation agent.

The reduction of the oxo group to a hydroxy group can be carried out by known methods. It is expedient, however, to accomplish the reduction of the starting material using an alkali-metal-metal hydride, such as lithium aluminum hydride or, especially, sodium borohydride, potassium borohydride and the like. A preferred method comprises carrying out the reduction using sodium borohydride in the presence of a solvent which is stable in the presence of the reducing agent. Suitable solvents include, for example, methanol, ethanol or dimethylformamide. After the reduction has been carried out any aralkyloxy group, especially the benzyloxy group, can be cleaved readily by hydrogenolysis to provide free hydroxy groups.

Such debenzylation is carried out advantageously, catalytically, for example, in the presence of a noble metal catalyst, such as palladium. In an additional procedural step, the compound can be esterified. The esters can be prepared by reacting with a conventional acylating agent.

Compounds of formula II are known or are analogous of known compounds and can be prepared by known methods.

Compounds of formula I can also be prepared by a known process, analogous to that described in U.S. Pat. No. 3,067, 203, which comprises cyclizing an acid amide of formula

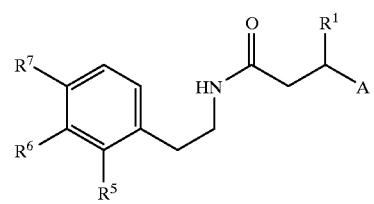

III wherein A, $R^1$ and $R^5$–$R^7$ are as described above, in the presence of an acid, preferably POCl$_3$, to the corresponding 1-phenyl-ethyl-3,4-dihydroisoquinoline derivative, which is subsequently reduced with a suitable reducing agent, such as an alkali metal-metal hydride, for example, sodium borohydride.

The compounds of formula IA can be prepared by a following reaction scheme, which shows a process which comprises cyclizing the acid amide of formula

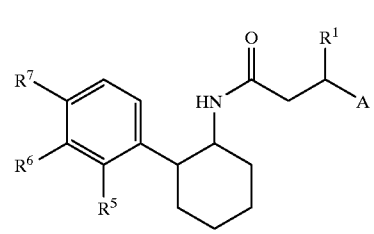

IV in the presence of an acid, preferably POCl$_3$, as described above for cyclizing the acid amide- of formula III.

SCHEME I

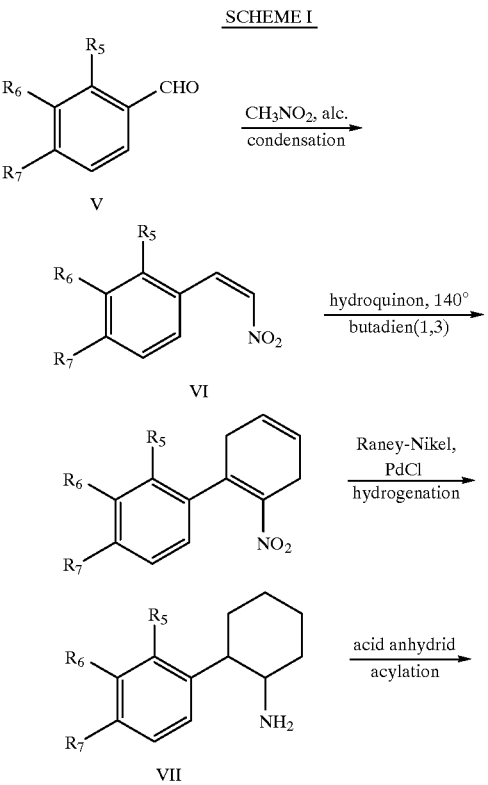

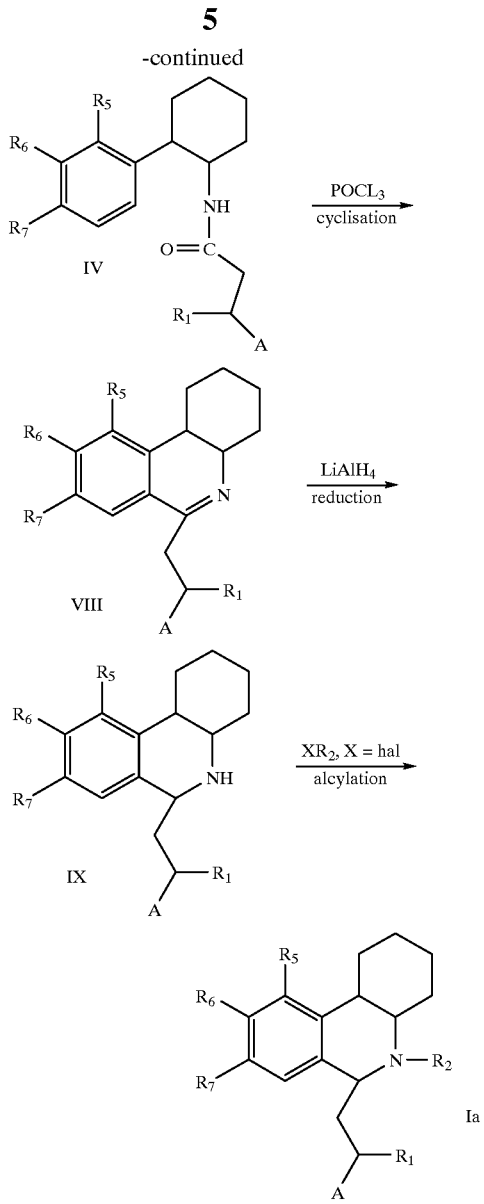

In Scheme I, $R_5$, $R_6$, $R_7$ and A are as described above. The compounds of formula V are known or can be prepared by known methods.

As described above, the tetrahydroisoquinolines of formula I contain two asymmetric carbon atoms and the formation of two stereoisomeric racemates is possible. If these racemates form concurrently, they can be separated by methods known per se, for example, by chromatography or by fractional crystallization. The racemates themselves, can, if desired, be separated into their optical antipodes by known methods, for example, by fractional crystallization of the salts with optically active acids, such as a-tartaric acid, dibenzoyl-α-tartaric acid or α-camphorsulfonic acid.

The compounds of formula I can be converted into pharmaceutically acceptable acid addition salts. These salts can be manufactured according to known methods.

The activity of compounds of formula I can be demonstrated by the following:

3H-MK801 (Dizocilpine) binding in vitro

The whole brain from 150–200 g male rats, without cerebellum and without medulla oblongata was dissected on ice. The tissue was then homogenized with an Ultra-Turrax maximum speed during 30 seconds at 4° C in 50 volumes of cold Tris HCl 50 mM, EDTA disodium 10 mM, pH=7.4 buffer (wet weight/v). The homogenate was centrifuged at 48'000 x g (20'000 rpm, SS34, Sorvall RC5C) for 10 minutes. The pellet was rehomogenized with the same volume of buffer and the homogenate incubated at 37° C for 10 minutes. After centrifugation as above, the pellet was rehomogenized with the same volume of buffer and frozen at −80° C. in 35 ml fractions for at least 16 hours and not more than 2 weeks.

For the binding experiment, the homogenate was centrifuged as above and the pellet was washed 3 times by homogenization in 25 volumes of cold Tris HCl 5 mM, pH=7.4 buffer (Ultra-Turrax, maximum speed, 30 seconds) and centrifugation as above. The final pellet was rehomogenized in 25 volumes of buffer (original wet weight) and used as such in the assay. The final concentration of membrane in the assay was 20 mg/ml (wet weight).

The incubation was performed in the presence of 1 nM glutamate, glycine and spermidine. MK-801, (+)-[3-3H(N)], NEN (NET-972) 20Ci/mmol, was used at 5 nM final concentration. Non specific binding was determined in presence of 100 mM TCP. After 2 hours of incubation at room temperature, the suspension was filtered (Whatmann GF/B, soaked in 0.1% polyethylenimine for 2 hours) and washed 5 times with 3 ml of cold Tris HCl 5mM, pH=7.4 buffer. The air-dried filters were counted with 10 ml of Ultima-gold (Packard) in a Tri-Carb 2500 TR scintillation counter after agitation.

The DPM were transformed in % of specific binding and these values were treated by a non linear regression calculation program (BINDING, H. Affolter, Switzerland) which provided the $IC_{50}$ values for the low and high affinity binding sites (=concentrations producing half maximal inhibition at the respective sites). Each experiment was repeated at least three times and the final $IC_{50}$ values were calculated as the mean +/-standard deviation of the individual experiments.

Reference: R. W. Ransom and N. L. Stec. Journal of Neurochemistry 51, 830–836, 1988.

Electrophysiology on recombinant NMDA receptors cDNA clones coding for the subunits NMDAR1C and NMDAR2A of the NMDA receptor (see Hollmann and Heinemann, 1994, Annu. Rev. Neurosci. 17: 31 for nomenclature of NMDA receptor subunits) were isolated from a rat brain λgtll cDNA library as published elsewhere (Sigel et al., 1994, J. Biol. Chem. 269:8204). The clone for the subunit NMDAR2B of the rat brain NMDA receptor was obtained from S.Nakanishi (Kyoto, Japan). The cDNAs were transcribed, capped and poly($A^+$)-tailed as described previously (Malherbe et al., 1990, Mol. Brain Res. 8: 199). Oocytes of South African frogs (Xenopus laevis) were used for expressing either a combination of the NMDAR1C and NMDAR2A subunits or the NMDAR1C and NMDAR2B subunits. Approximately 3 fmol of a 1:1 mixture of the respective mRNA species were injected into every oocyte. Four to five days later the ion current through the NMDA receptor channels was measured in voltage clamp experiments (see Methfessel et al., 1986, Pflügers Arch. 407: 577 for the methods of oocyte expression and voltage-clamping). The membrane potential was clamped to −80 mV and the receptors were activated by applying a modified Ringer's solution containing the agonists L-asparatate (Asp) and glycine (Gly). Different agonist concentrations were chosen for either subunit combination to account for the different agonist sensitivities of the two types of receptors (70 μM Asp plus 2.5 μM Gly for NMDAR1C—NMDAR2A and 15

μM Asp plus 0.2 μM Gly for NMDAR1C—NMDAR2B). The agonists were applied for 15 second intervals once every 2.5 minutes by rapid superfusion of the oocyte. After a series of initial control stimuli increasing concentrations of the antagonist to be tested were added to both, the basal Ringer's and the agonist containing solution. For the data analysis the amplitude (y) of the agonist-induced current was plotted versus the concentration (x) of the antagonist and the logistic function $y=A/[1+(x/IC_{50})^H]$ was fitted to the data to estimate the 50% inhibitory concentration ($IC_{50}$). Three to six oocytes were tested for every antagonist and if possible, at least 3 concentrations embracing the $IC_{50}$ were applied to every oocyte. However, concentrations higher than 100 μM were never used even if the $IC_{50}$ had not yet been reached at 100 μM and for two compounds the maximum concentration was even less (20–30 μM) because of limited solubility. In these cases a lower limit (e.g., ">100 μM") for the $IC_{50}$ is given in table "Test Results". In two other cases a concentration of 0.1 μM produced a slowly increasing block which exceeded 50% after 30 min. Because of the slow onset of block it was unreasonable to test even lower concentrations; instead an upper limit ("<0.1 μM") for the $IC_{50}$ is given in table "Test results". Figures for the $IC_{50}$ in all other cases are arithmetic mean values of individual $IC_{50}$s determined by the logistic curve fits.

Tested compounds of formula I

| Nr. | A | $R^1$ | $R^2$ | $R^3$ | $R^4$ | $R^5$ | $R^6$ | $R^7$ |
|---|---|---|---|---|---|---|---|---|
| A | —⟨C6H4⟩—CH3 | OH | $CH_3$ | H | H | H | $OCH_3$ | $OCH_3$ |
| B | —⟨C6H4⟩—Cl | H | $CH_3$ | H | H | H | $OCH_3$ | OH |
| C | —⟨C6H4⟩—Cl | OH | $CH_3$ | H | H | H | $OCH_3$ | $OCH_3$ |
| D | —⟨C6H4⟩—Cl | H | $CH_3$ | H | H | H | OH | OH |
| E | —⟨C6H4⟩—CH3 | H | $CH_3$ | H | H | H | $OCH_3$ | $OCH_3$ |
| F | —⟨C6H4⟩—Cl | H | $CH_3$ | together —$(CH_2)_4$— | | H | $OCH_3$ | $OCH_3$ |
| G | —⟨C6H4⟩—NO2 | OH | $CH_3$ | H | H | H | $OCH_3$ | $OCH_3$ |
| H | —⟨C6H4⟩—Cl | H | H | together —$(CH_2)_4$— | | H | $OCH_3$ | $OCH_3$ |
| I | —⟨C6H4⟩—OCH3 | OH | $CH_3$ | H | H | H | $OCH_3$ | $OCH_3$ |

-continued
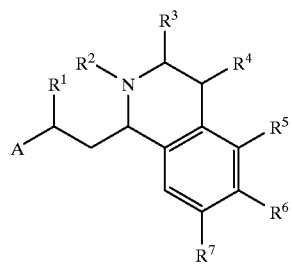
| Nr. | A | R¹ | R² | R³ | R⁴ | R⁵ | R⁶ | R⁷ |
|---|---|---|---|---|---|---|---|---|
| J | 4-Cl-C₆H₄ | H | CH₃ | H | H | H | OCH₃ | OCH₃ |
| K | 2,4,5-tri-Cl-C₆H₂ | OH | CH₃ | H | H | H | OCH₃ | OCH₃ |
| L | 4-Br-C₆H₄ | H | CH₃ | H | H | H | OCH₃ | OCH₃ |
| M | 4-OCH₃-C₆H₄ | H | CH₃ | H | H | H | OCH₃ | OCH₃ |
| N | 4-iPr-C₆H₄ | H | CH₃ | H | H | H | OCH₃ | OCH₃ |
| O | 4-NO₂-C₆H₄ | H | CH₃ | H | H | H | OCH₃ | OCH₃ |
| P | 4-Cl-C₆H₄ | H | CH₃ | H | H | H | together —O—CH₂—O— | |
| Q | 4-Cl-C₆H₄ | —O—C(=O)—CH₃ | CH₃ | H | H | H | OCH₃ | OCH₃ |
| R | C₆H₅ | H | CH₃ | H | H | H | OCH₃ | OCH₃ |
| S | 4-Cl-C₆H₄ | —O—C(=O)—CH₂CH₃ | CH₃ | H | H | H | OCH₃ | OCH₃ |
| T | 3,4-di-Cl-C₆H₃ | H | CH₃ | H | H | H | OH | OH |

-continued

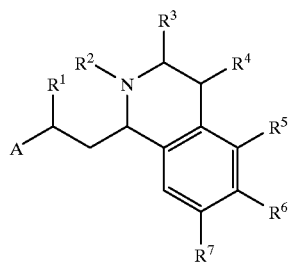

| Nr. | A | R¹ | R² | R³ | R⁴ | R⁵ | R⁶ | R⁷ |
|---|---|---|---|---|---|---|---|---|
| U | 4-NO₂-phenyl | H | $CH_3$ | H | H | H | $OCH_3$ | $OCH_3$ |
| V | 4-Cl-phenyl | OH | $CH_3$ | H | H | H | $OCH_3$ | $OCH_3$ |
| W | 4-Cl-phenyl | H | $CH_3$ | H | H | $OCH_3$ | $OCH_3$ | H |
| X | 4-Cl-phenyl | H | $CH_3$ | $CH_3$ | H | H | $CH_3$ | $CH_3$ |
| AA | 3,4-diCl-phenyl | H | $CH_3$ | H | H | H | $OCH_3$ | $OCH_3$ |

Test results

| | 3H-MK 801/$IC_{50}$ ($\mu M$) | | Electrophysiology/$IC_{50}$ ($\mu M$) oocytes | |
|---|---|---|---|---|
| Compound | high | low | NMDAR 1C & 2A | NMDAR 1C & 2B |
| A | 0.04 | 223 | >100 | ≦0.1 |
| B | 0.09 | 54 | 15 | 0.49 |
| C | 0.12 | 191 | >20 | 0.043 |
| D | 0.29 | 116 | 19 | 0.28 |
| E | 0.34 | 129 | | |
| F | 0.4 | 315 | >30 | <0.1 |
| G | 0.46 | 87 | | |
| H | 0.5 | 589 | | |
| I | 0.59 | 146 | | |
| J | 0.6 | 107 | | |
| K | 0.91 | 613 | | |
| L | 1.37 | 198 | | |
| M | 1.39 | 95 | | |
| N | 1.59 | 370 | | |
| O | 1.6 | 101 | | |
| P | 1.7 | 95 | | |
| Q | 1.76 | 161 | 21 | 1.2 |
| R | 2.1 | 147 | | |
| S | 2.18 | 123 | | |
| T | 2.31 | 56 | | |
| U | 2.71 | 87 | | |
| V | 2.9 | 110 | | |
| W | 3.6 | 129 | | |
| X | 3.87 | 2233 | | |
| Y | 3.9 | 93 | | |
| Z | 4.1 | 135 | | |
| AA | 4.62 | 185 | | |

The above tests show that compounds of formula I are NMDA receptor subtype selective blockers. For selected compounds the preference for NMDAR-2B subunits could be demonstrated by electrophysiological characterization using cloned NMDA receptor subtypes expressed in oocytes.

The compounds of formula I and their salts can be incorporated into standard pharmaceutical dosage forms, for example, for oral or parenteral application with the usual pharmaceutical adjuvant materials, for example, organic or inorganic inert carrier materials, such as, water, gelatin, lactose, starch, magnesium stearate, talc, vegetable oils, gums, polyalkylene-glycols and the like. The pharmaceutical preparations can be employed in a solid form, for example, as tablets, suppositories, capsules, or in liquid form, for example, as solutions, suspensions or emulsions. Pharmaceutical adjuvant materials can be added and include preservatives, stabilizers, wetting or emulsifying agents, salts to change the osmotic pressure or to act as buffers. The pharmaceutical preparations can also contain other therapeutically active substances.

The daily dose of compounds of formula I to be administered varies with the particular compound employed, the chosen route of administration and the recipient. Representative of a method for administering the compounds of formula I is by the oral and parenteral type administration route. An oral formulation of a compound of formula I is preferably administered to an adult at a dose in the range of 150 mg to 1.5 mg per day. A parenteral formulation of a compound of formula I is preferably administered to an adult at a dose in the range of from 5 to 500 mg per day.

The invention is further illustrated in the following examples.

EXAMPLE 1

Tablet Formulation (Wet Granulation)

| Item Ingredients | mg/tablet | | | |
|---|---|---|---|---|
| | 5 mg | 25 mg | 100 mg | 500 mg |
| 1. 2-(6,7-Dimethoxy-2-methyl-1,2,3,4-tetrahydroisoquinolin-1-yl)-1-p-tolyl-ethanol | 5 | 25 | 100 | 500 |
| 2. Lactose Anhydrous DTG | 125 | 105 | 30 | 150 |
| 3. Sta-Rx 1500 | 6 | 6 | 6 | 30 |
| 4. Microcrystalline Cellulose | 30 | 30 | 30 | 150 |
| 5. Magnesium Stearate | 1 | 1 | 1 | 1 |
| TOTAL | 167 | 167 | 167 | 835 |

Manufacturing Procedure:
1. Mix Items 1, 2, 3 and 4 and granulate with purified water.
2. Dry the granulation at 50° C.
3. Pass the granulation through suitable milling equipment.
4. Add Item 5 and mix for three minutes; compress on a suitable press.

EXAMPLE 2

Capsule Formulation

| Item Ingredients | mg/capsule | | | |
|---|---|---|---|---|
| | 5 mg | 25 mg | 100 mg | 500 mg |
| 1. 2-(6,7-Dimethoxy-2-methyl-1,2,3,4-tetrahydroisoquinolin-1-yl)-1-p-tolyl-ethanol | 5 | 25 | 100 | 500 |
| 2. Hydrous Lactose | 159 | 123 | 148 | — |
| 3. Corn Starch | 25 | 35 | 40 | 70 |
| 4. Talc | 10 | 15 | 10 | 25 |
| 5. Magnesium Stearate | 1 | 2 | 2 | 5 |
| TOTAL | 200 | 200 | 300 | 600 |

Manufacturing Procedure:
1. Mix Items 1, 2, and 3 in a suitable mixer for 30 minutes.
2. Add Items 4 and 5 and mix for 3 minutes.
3. Fill into a suitable capsule.

EXAMPLE 3

Tablet Formulation (Wet Granulation)

| Item Ingredients | mg/tablet | | | |
|---|---|---|---|---|
| | 5 mg | 25 mg | 100 mg | 500 mg |
| 1. 2-(6,7-Dimethoxy-2-methyl-1,2,3,4-tetrahydroisoquinolin-1-yl)-1-p-tolyl-ethanol | 5 | 25 | 100 | 500 |
| 2. Lactose Anhydrous | 125 | 105 | 30 | 150 |
| 3. Sta-Rx 1500 | 6 | 6 | 6 | 30 |
| 4. Microcrystalline Cellulose | 30 | 30 | 30 | 150 |
| 5. Magnesium Stearate | 1 | 2 | 2 | 5 |
| TOTAL | 167 | 167 | 167 | 835 |

Manufacturing Procedure:
1. Mix Items 1, 2, 3 and 4 and granulate with purified water.
2. Dry the granulation at 50° C.
3. Pass the granulation through suitable milling equipment.
4. Add Item 5 and mix for three minutes; compress on a suitable press.

We claim:
1. A method for the control or treatment of diseases caused by overreaction of NMDA-R receptor subtypes which comprises administering to a host in need of such treatment an effective amount of a compound of the formula

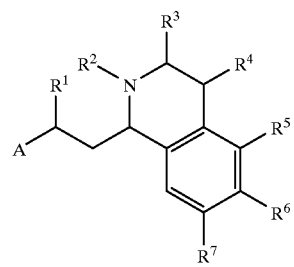

I wherein

A is waryl hich is unsubstituted or substituted by one or two or three substituents indepedently selected from lower alkyl, halogen or nitro $R^1$ is hydrogen, hydroxy, lower alkyl, lower alkoxy, R—CO— or R—COO—, wherein R is lower alkyl;

$R^2$ is lower alkyl or cycloalkyl $R^3$–$R^7$ are, independently, hydrogen, lower alkyl, lower alkoxy, hydroxy or $R^6$ and $R^7$ taken together are —OCH$_2$O— or a pharmaceutically acceptable salt.

2. A method according to claim 1, wherein $R^1$ is hydrogen or hydroxy.

3. A method according to claim 1, wherein $R^2$ is lower alkyl or hydrogen.

4. A method according to claim 1, wherein $R^3$ and $R^4$ are hydrogen.

5. A method according to claim 1, wherein $R^6$ and $R^7$ are lower alkoxy or hydroxy.

6. A method according to claim 1, wherein the compound of formula I is 2-(6,7-dimethoxy-2-methyl-1,2,3,4-tetrahydroisoquinolin-1-yl)-1-p-tolyl-ethanol.

7. A method according to claim 1, wherein the compound of formula I is 1-[2-(4-chloro-phenyl)-ethyl]-6-methoxy-2-methyl-1,2,3,4-tetrahydro-isoquinolin-7-ol.

8. A method according to claim 1, wherein the compound of formula I is 1-(4-chloro-phenyl)-2-(6,7-dimethoxy-2-methyl-1,2,3,4-tetrahydroisoquinolin-1-yl)-ethanol.

9. A method according to claim 1, wherein the compound of formula I is 1-[2-(4-chloro-phenyl)-ethyl]-2-methyl-1,2,3,4-tetrahydro-isoquinline-6,7-diol.

10. A method according to claim 1, wherein the compound of formula I is 6,7-dimethoxy-2-methyl-1-(2-p-tolyl-ethyl)-1,2,3,4-tetrahydroisoquinline.

11. A method according to claim 1, wherein the compound of formula I is 2-(6,7-dimethoxy-2-methyl-1,2,3,4-tetrahydroisoquinlin-1-yl)-1-(4-nitro-phenyl)-ethanol.

* * * * *

UNITED STATES PATENT AND TRADEMARK OFFICE
CERTIFICATE OF CORRECTION

PATENT NO. : 5,952,344
DATED : September 14, 1999
INVENTOR(S) : Alanine, et al.

It is certified that error appears in the above-identified patent and that said Letters Patent is hereby corrected as shown below:

Claim 1, Column 14, line 41: "A is waryl hich" should read --- A is aryl which --- .

Signed and Sealed this

Twenty-ninth Day of February, 2000

*Attest:*

Q. TODD DICKINSON

*Attesting Officer*     *Commissioner of Patents and Trademarks*

UNITED STATES PATENT AND TRADEMARK OFFICE
CERTIFICATE OF CORRECTION

PATENT NO. : 5,952,344
DATED : September 14, 1999
INVENTOR(S) : Alanine, et al.

It is certified that error appears in the above-identified patent and that said Letters Patent is hereby corrected as shown below:

Claim 1, Column 14, line 41: "A is waryl hich" should read --- A is aryl which --- .

Signed and Sealed this

Eighth Day of August, 2000

Attest:

Q. TODD DICKINSON

Attesting Officer

Director of Patents and Trademarks